(12) United States Patent
Peuker et al.

(10) Patent No.: US 6,715,645 B2
(45) Date of Patent: Apr. 6, 2004

(54) MIXING CAPSULE AND METHOD OF MAKING AND USING SAME

(75) Inventors: Marc Peuker, Seefeld (DE); Michael Sick, Schondorf (DE); Klaus-Peter Stefan, Seefeld (DE); Gabriele Hager, Augsburg (DE); Angela Stenger, Gruewald (DE); Gunther Eckhardt, Frieding (DE)

(73) Assignee: 3M ESPE AG, Seefeld (DE)

( * ) Notice: Subject to any disclaimer, the term of this patent is extended or adjusted under 35 U.S.C. 154(b) by 0 days.

(21) Appl. No.: 10/204,250
(22) PCT Filed: Feb. 15, 2001
(86) PCT No.: PCT/EP01/01646
  § 371 (c)(1),
  (2), (4) Date: Nov. 27, 2002
(87) PCT Pub. No.: WO01/62175
  PCT Pub. Date: Aug. 30, 2001

(65) Prior Publication Data
  US 2003/0136799 A1 Jul. 24, 2003

(30) Foreign Application Priority Data
  Feb. 21, 2000 (DE) .......................... 100 07 581

(51) Int. Cl.⁷ ................................ B67D 5/36
(52) U.S. Cl. .................. 222/129; 222/145.1; 222/1
(58) Field of Search .................. 222/1, 129, 145.1, 222/327, 386, 541.1, 541.3

(56) References Cited

U.S. PATENT DOCUMENTS

| | | | | |
|---|---|---|---|---|
| 3,796,303 A | * | 3/1974 | Allet-Coche | 206/220 |
| 3,907,106 A | | 9/1975 | Purrmann et al. | 206/219 |
| 6,387,073 B1 | * | 5/2002 | Weiler et al. | 604/87 |

FOREIGN PATENT DOCUMENTS

| | | |
|---|---|---|
| DE | 32 24 296 | 12/1973 |
| DE | 36 35 574 | 4/1988 |
| DE | 93 03 268 | 8/1994 |
| EP | 0 759 286 | 2/1997 |
| WO | WO 00/30953 | 6/2000 |

\* cited by examiner

Primary Examiner—Gene Mancene
Assistant Examiner—M A Cartagena
(74) Attorney, Agent, or Firm—Crowell & Moring LLP

(57) ABSTRACT

The invention relates to a mixing capsule, especially for producing dental materials. The inventive capsule is provided with a cartridge which is closed on one end thereof by means of a piston. A hemispherical cavity is configured in the piston. Said cavity forms an additional chamber and is closed in relation to the main chamber of the cartridge by means of a separating device. A body that is present in the main chamber in the initial state serves for supporting the mixing process and for chopping through the separating device at the beginning of the mixing process in such a way that the main chamber and the additional chamber form a coherent mixing chamber. The body enters the hemispherical additional chamber and acts as a displacing body at the end of the output process. The mixing capsule is provided with a coding.

36 Claims, 2 Drawing Sheets

MIXING CAPSULE AND METHOD OF MAKING AND USING SAME

BACKGROUND AND SUMMARY OF THE INVENTION

The present invention relates to a mixing capsule and to a mixer unit which includes a mixing capsule, in particular for the production of a dental material which preferably contains a plurality of components.

Mixing capsules which are filled with the components in separate chambers by the manufacturer are used to produce mixtures of two or more components. The components are brought into communication and mixed with one another by the user, for example by destroying a wall separating the chamber.

Mixing capsules for the production of dental materials which are often mixed from a pulverulent component and a liquid component, the mixing procedure usually taking place in a shaker unit, are known in the dental sector. The fully mixed substance is then dispensed directly onto the working area, for example into a tooth cavity, through a dispensing spout formed integrally on the mixing capsule.

DE 36 35 574 A discloses a mixing capsule intended for the production of jointing and sealing compounds. In an illustrative embodiment described in said document, an auxiliary chamber which is present in the dispensing piston is delimited, on the side facing the main chamber of the capsule, by a foil and, on the opposite side, by an auxiliary piston which is arranged displaceably in the dispensing piston. In the initial state of the mixing capsule, in addition to the second component, a mixer body is accommodated in the auxiliary chamber, which mixer body initially serves to destroy the foil by means of manual displacement of the auxiliary piston and then assists in the mixing procedure. To allow the reduction in volume which is necessary for displacement of the inner piston together with ball, a gas cushion is provided in the mixing chamber.

In a further embodiment of the known mixing capsule, the mixing ball is initially situated in the main chamber. In this case, the auxiliary chamber present in the piston is closed off from the main chamber by means of a cover and on its rear side by a bellows. As a result of manual pressure being applied to the bellows, the cover is pressed away from the piston, so that the two chambers are brought into communication for the purpose of activating the capsule.

In both cases, a dedicated working step which has to be carried out manually is required for activation of the capsule. Furthermore, a gas cushion is required in order to permit the reduction in volume which is required for removal of the cover.

In a multicomponent mixing capsule for dental purposes which is known from DE 94 00 374 U1, a first component is contained in a mixing chamber and a second, liquid component is contained in a foil bag which is arranged in an auxiliary chamber which is separated from the mixing chamber by a displaceable wall element. A cylindrical mixing body which is present in the mixing chamber is used to displace the wall element at the start of the mixing procedure and thus to compress the foil bag, so that the latter bursts open and releases the liquid component through a liquid passage which is present in the wall element.

One difficulty with this device lies in designing the wall element, the film bag and the capsule itself in such a way, and in dimensioning these components with sufficiently low tolerances, for the wall element to be held in its starting position while the capsule is being stored and transported but to be displaced sufficiently far and with such force, under the action of the mixing body, that the foil bag bursts open. In this context, it should be borne in mind that the fact that the foil bag is often only partially emptied leads to undesirable changes in the mixing ratio and therefore to deterioration in the properties of the finished mixture. Another drawback is that this arrangement is suitable only for mixing, but not for application of the paste.

DE 93 03 268 U1 describes a multicomponent mixing capsule with ejection device for a mixed compound, primarily for dental purposes. This mixing capsule has an activation mandrel which is located in the interior of the capsule and is anchored against the direction of ejection by means of holders in the interior of the capsule body, and a liquid compartment which is accommodated in the interior of a ram and is sealed off with respect to the activation mandrel by a destructible membrane. The activation mandrel fits flush into the empty vessel in the interior of the ram and seals the latter while the material is being forced out.

While the material is being forced out in the longitudinal direction, the liquid passes through the thin capillary, which comes to lie in the interior of the activation mandrel, into the mixing space. It is explained that, even during the mixing operation in a vibration mixer and during the dispensing of the compound via the ejection nozzle, a small residue of liquid, which is not precisely reproducible, always remains in the capillary. This impairs the quality of the results of mixing.

A comparable mixing capsule is described in WO 00/30953.

The object of the present invention can primarily be regarded as that of making available an improved mixing capsule which avoids the abovementioned problems without impairing the desired results of mixing.

A further object can be regarded as that of making available a method for mixing and dispensing mixtures from mixing capsules, which method requires a smaller number of steps.

This object is achieved by a mixing capsule and a method for producing a mixing capsule as described in the claims.

The words "comprise" or "include" within the meaning of the invention precede a nonexhaustive list of features. The word "one" is to be interpreted as an indefinite quantity with the meaning of "at least one".

The mixing capsule according to the invention has, inter alia, the following advantages:

The movable body which is present in the mixing capsule serves not only to activate the capsule by destroying the separating device and to assist in the mixing procedure, but also serves as a displacement body during emptying.

The mixing capsule according to the invention also permits reproducible mixing of highly viscous substances.

Since, in the initial state, the body is situated in the main chamber, the activation preferably takes place automatically at the start of the mixing procedure, in contrast to the activation steps, known from the prior art, which have to be carried out manually.

Since, furthermore, the auxiliary chamber is separated from the main chamber by the separating device through which the body can penetrate, during the subsequent mixing procedure it forms part of the mixing chamber itself. This ensures that the second component included in the auxiliary chamber completely enters the mixture which is being formed.

Moreover, the unification of main chamber and auxiliary chamber advantageously increases the available mixing volume.

In the final phase of the dispensing procedure, the body assists in the virtually complete emptying of the mixing capsule interior formed by the main chamber and auxiliary chamber.

A further advantage is the small number and simple design of the components of the mixing capsule.

An advantage over the mixing capsule known for example from DE 23 24 296 A is that, because there is no need to arrange a foil cushion on the outside of the cartridge, together with a clasp for holding it, the capsule can have a smaller radial diameter with the same volume. This makes it easier to apply the mixture or compound from the capsule into a cavity of a tooth.

As appropriate, a plurality of freely movable bodies are located in the mixing capsule.

The movable body is preferably of spherical configuration. The diameter of the sphere is preferably in the range of 4 to 10 mm, particularly preferably in the range of 5 to 8 mm.

However, any other configuration of the body is also conceivable, for example an egg-shaped or lens-shaped configuration, or a configuration in the form of a platonic body. Depending on the chosen separating layer, such a configuration can more easily destroy the separating layer and, as appropriate, permits a smaller mass and/or size of the body.

The configuration of a body with corners and edges can also be favorable for dispensing the mixture from the capsule. Such a body cannot fit uniformly into the auxiliary chamber. There are therefore different width distances between the surface of the body and the inner surface of the auxiliary chamber. These facilitate the flow of the mixture when dispensing in the direction of the dispensing spout.

It can also be advantageous for the body to be designed in a ring shape. Depending on the size of the ring, the latter can engage to a greater or lesser extent into the auxiliary chamber and act there as a displacement body.

In a further embodiment, the piston is configured in such a way that it can deform, in particular plastically deform, during dispensing.

This can be achieved by the fact that the piston, which has at least one auxiliary chamber, consists of a deformable material or comprises such a material.

Another expedient configuration is one which has a geometric shape which facilitates the deformation.

A configuration of the piston which has proven expedient is one in the form of a hollow piston open at both ends with a first indent and a second indent, the first indent forming, together with the separating device, the auxiliary chamber.

Such a form can be obtained, for example, by pushing in the bottom surface of a beaker made of a deformable material. The pressing-in is preferably done using a ram.

It is also conceivable for such a piston to be produced by injection-molding or thermoforming of a deformable material.

For better sealing of the piston against the capsule wall, the piston preferably has one or more sealing lips.

An additional sealing action can be obtained by a configuration which, during the application procedure, allows the collapsible piston to spread open and press against the capsule wall.

Among others, the combination of a lens-shaped body in conjunction with a deformable piston has proven expedient.

To ensure more complete dispensing of the mixture from the mixing capsule, it can also be advantageous to arrange a projection on the outside of the piston base. Such a projection can be in the form of a thickened part of the piston base or in the form of a spacer piece, which is preferably cylindrical.

Since an application device having a displaceable piston rod and a ram with a defined and commercially standardized length is needed for dispensing the mixture, it is in some cases necessary to lengthen the axial length of the ram beyond the projection. In this way it is possible to ensure that the deformable piston can be displaced into the area of the dispensing spout. Another advantage is that there is less risk of the piston rod or the ram of the application device being jammed upon deformation of the piston of the mixing capsule.

The weight of the movable body is adapted to the nature of the separating device in such a manner that, during normal transport and normal handling, the separating device is not damaged by the movable body. The separating device can only be penetrated once acceleration values of, for example, 100–500 g (1 g=9.81 ms$^{-2}$), preferably 200–400 g, which customarily occur in capsule mixer units, are reached.

Materials which are usable for the ball or body have a density in the range of 2 to 12 g/cm$^3$. The mass of the ball usually lies in the range of 0.1 to 10 g, preferably in the range of 0.3 to 3.0 g.

The shape of the auxiliary chamber is preferably essentially a hemisphere with a radius which is slightly larger than that of the body. This is favorable for the mixing capsule to be emptied with the minimum possible amount of residues. It can also be advantageous for the emptying of the mixing capsule, particularly in the case of highly viscous material, if the auxiliary chamber has channel-like depressions, for example in the form of grooves. These depressions preferably extend from the bottom of the auxiliary chamber in the direction toward the end face of the auxiliary chamber.

The total volume of the mixing capsule available for mixing is usually in the range of 0.5 to 5 ml, in particular 1 to 3 ml. The volume of the auxiliary chamber is preferably smaller than the volume of the main chamber. The volume of the auxiliary chamber is usually 0.05 ml to 0.5 ml, preferably 0.1 to 0.3 ml.

As appropriate, the maximum diameter of a body deviating from the ball shape, for example in a form with corners and edges, can also be slightly greater than the diameter of the auxiliary chamber. This embodiment is useful in particular when the body is made of a deformable material or comprises such a material. In this case, during activation of the mixing capsule, the body moving relative to the mixing capsule will be deformed by the rapid movement in such a way that it can finally pass as a displacement body into the auxiliary chamber during the dispensing procedure.

Making the body from a deformable material is also expedient to the extent that at the outset, before activation of the mixing capsule, the body can have an edged configuration which during activation initially facilitates the opening of the separating device. During the mixing procedure, the body finally assumes an increasingly rounded configuration which can more readily pass into the auxiliary chamber, but on the other hand leads to much less abrasion of the foil.

It is advantageous if the separating device adheres to an annular surface of the piston, delimiting the auxiliary chamber, and the transition between the annular surface and the inner wall of the auxiliary chamber has a sharp-edged region.

This sharp-edged region preferably runs over a part of the circumference, preferably over substantially 60° to 120°, particularly preferably from 70° to 90°. The transition between annular surface and the inner wall of the auxiliary chamber is preferably rounded in the remaining region. This embodiment prevents the foil from tearing off altogether.

In a particular embodiment, the separating device has a desired breaking point which, independently of the nature of the above-described edge region, contributes to controlled and reliable opening of the auxiliary chamber. The prior damage of the separating device or preparation of a desired breaking point can be effected, for example, by radiation, such as laser radiation, mechanically by scoring or incision using a blade, or thermally by partial fusion or scoring using a heatable blade.

The preparation is preferably carried out only on the plastic part, which may be present, of the separating device, i.e. on the substrate material which is present on one or both sides of a metal layer or $SiO_x$-containing layer. As a result, the seal of the optionally present metal-containing or $SiO_x$-containing layer is maintained.

The preparation can be of any desired shape, but is preferably in a shape which prevents the separating device or parts of this device from tearing off after or during penetration of the separating device by the body.

It has proven expedient for the separating device to be prepared in the form of two or more lines which cross one another in the axis of symmetry of the capsule.

In this case, the separating layer only bursts open at a defined location. This prevents the separating layer or parts of this layer from entering the mixture and impeding the dispensing procedure.

A star-shaped preparation with branching arms can also be used. Such a preparation facilitates the mixing procedure since wedge-shaped foil parts of the separating device in the region of the wall of the auxiliary chamber have a shorter chord length, by which means the component parts of the foil can be more easily turned back during mixing.

Another expedient preparation is one in which a foil part has the outline of a skittle, the head of the skittle being of circular shape and its center point being located on the longitudinal axis of the cartridge. This preparation too facilitates the substantially complete opening of the separating device and thus the access to the auxiliary chamber.

Suitable preparations of the separating device are shown in the figures.

A further advantage of such desired breaking points is that even relatively thick foils, including multilayer foils, in the range from 50 to 80 µm, preferably 60 to 70 µm, can be penetrated with little force (lower mass of the body).

The separating device is preferably in the form of a single-layer or multilayer foil, particularly preferably in the form of a composite foil or a sealing foil. A three-layer foil comprising a plastic outer layer, at least one barrier layer, preferably of plastic, and a sealing layer has proven useful, in which case the sealing layer can also be a plastic foil or a sealing resin.

The foil preferably comprises at least one metal layer, such as an aluminum layer and/or gold layer, and at least one plastic layer, possibly two, three or more plastic layers.

Examples of suitable plastics are: PE, PP, PET, PTFE, PVC, polyamides.

Furthermore, instead of or in addition to the metal foil, the separating device can have plasma-polymerized layers, such as hydrocarbon-containing layers or ceramic barrier layers, such as $SiO_x$ layers.

The separating device is attached to the annular end face of the piston, for example by heat-sealing, adhesive bonding, ultrasonic welding or high-frequency welding.

Examples of layers suitable as the outer layer are those comprising PET, PP, PE and/or PA, examples of layers suitable as the barrier layer are those comprising Al and/or SiOx, and examples of layers suitable as the sealing layer are those comprising HDPE, LDPE and/or PP. A coating of PET/Al/LDPE or PA/Al/LDPE has proven expedient.

The layer thicknesses of the individual foils (outer layer, barrier layer, sealing layer) lie in the range of 5 to 60 µm, preferably from 8 to 50 µm.

In order to receive a third component, the separating device can moreover be designed in the form of a foil cushion.

Alternatively, a foil cushion for receiving a third component can be secured on the outer wall of the mixing capsule. It can be secured via a flexible clasp or by gluing. In this embodiment, the outer wall of the mixing capsule is provided with a bore through which the third component can be introduced into the main chamber. The transfer of the third component is preferably effected by applying pressure on the outer foil cushion. The foil cushion, which is arranged on the bore in order to seal the latter, bursts in the area of the bore and empties its content into the main chamber. A comparable embodiment is described in DE 23 24 296 A.

Advantageous materials for the piston of the mixing capsule include metals, such as anodized aluminum, glass, ceramic such as zirconia, plastics and/or—to reduce permeability—plastics which are optionally metalized or have undergone vapor deposition or coating with other materials which have a barrier action. Examples of possible plastics include: PE, PP, PET, PTFE, PVC, EVA, polyamides.

Furthermore, combinations of the abovementioned materials, such as a metal insert, preferably made of aluminum, which is surrounded on the outside and on the inside by the plastic, are conceivable. Parts of this type can be produced using the injection-molding process.

The piston can be produced in a two-component injection-molding process. In this process, first of all, by way of example, an inlay is produced, around which, by way of example, PE is then injection-molded.

Nonabrasive materials such as high-density plastics, for example PTFE, inorganic materials with optionally ceramic properties, such as glass, alumina or zirconia, metals such as Fe, Ti, V, Al or stainless steel are suitable for the body of the mixing capsule. The body can be coated with plastic; coatings with PE, PP, PA, PTFE, silicone-containing plastics and/or titanium nitrite have proven expedient.

The components which are contained in the main chamber, the auxiliary chamber and/or, if appropriate, in the separation device, or the foil cushion arranged separately on the outer wall of the mixing capsule, include both liquids and solids, preferably in powder or granule form. However, base substances in paste form are also possible.

In order to avoid damping of the freely movable body by the substances located in the main chamber during the activation procedure, it can also be expedient for these substances to be present in pressed form. The pressed article is preferably located between the end face of the cartridge and the body.

The solids comprise inert fillers, such as finely ground quartz, $SiO_x$-containing substances, glass materials, reactive fillers of all kinds, it being possible for the solids to be surface-modified.

The liquids comprise in particular matrix-forming polymerizable substances, for example polyacids comprising acrylic acid derivatives, methacrylic acid derivatives and maleic acid derivatives, as well as copolymers thereof.

The mixing capsule is preferably suitable for storing, mixing and dispensing glass ionomer cements.

The dispensing spout on the mixing capsule can be fitted eccentrically on the main chamber. It can also be advantageous to form one or more channels which open into the dispensing spout. A design of this type can be expedient for undisturbed emptying of the mixing capsule.

Furthermore, the dispensing spout is preferably of closable design. Possible embodiments are described, for example, in EP-A-0 157 121 A, in which the dispensing spout is pivotably mounted so that it is closed or open depending on the position of the dispensing spout. It is also contemplated to use a spout displacement cap in order to close the dispensing spout.

The mixing capsule has a coding. Suitable codings are, for example, colored identifiers, for example in the form of colored rings, labels, imprints or electronically readable codes (barcodes). It is also contemplated to provide a plurality of codings. The coding can contain information concerning the mixing time, the material, the manufacturer and/or the expiry date.

Coding of the mixing capsule, or of the substances contained therein, using a colored design of the dispensing spout is particularly advantageous if photosensitive substances are intended to be stored in the mixing capsule. To protect these from incident light, it is often necessary for the piston and/or the cartridge to be colored black. If differently colored substances are to be stored in the cartridge, these substances can no longer be identified through the color of the black piston and/or cartridge.

The color identification or coloring is preferably obtained by two-component injection-molding (two-component injection-molding process) of dispensing spout and cartridge. This is linked with a reduction in the number of parts of the capsule and in a reduction in costs in the manufacturing process.

The piston can also have a deformable, damping geometry in order to attenuate the noise which is caused by the body during activation in a suitable mixer unit. This can be achieved, for example, by providing an annular raised portion, possibly tapering to a point, at the end of the piston.

The invention also relates to a method for mixing and dispensing mixtures from mixing capsules, comprising the following steps:

a) provision of a mixing capsule with at least two chambers in which components of the mixture are stored separated from one another by a separating device, comprising a cartridge, a piston arranged displaceably in the cartridge, a dispensing spout, and at least one freely movable body which can penetrate the separating device and can pass as a displacement body into one of the chambers during the dispensing procedure, b) insertion of the mixing capsule into a mixer unit with a capsule holder, c) acceleration of the mixing capsule preferably by rapid translational and/or rotary movement, as a result of which the at least two chambers separated by a separating device are opened to form one mixing space, d) removal of the mixing capsule from the mixer unit, e) displacement of the piston by using an application device with a piston rod, as a result of which the mixture produced in step c) is applied onto or into a surface, in particular a hard dental tissue or a tooth cavity, via the dispensing spout of the mixing capsule.

A customary application device comprises a holder for insertion of the mixing capsule and a displaceable piston rod which is dimensioned so that it can move the piston of the mixing capsule in the direction of the dispensing opening.

BRIEF DESCRIPTION OF THE DRAWINGS

Preferred illustrative embodiments of the mixing capsule are explained below with reference to the drawings.

DETAILED DESCRIPTION OF THE DRAWINGS

Figure 4:
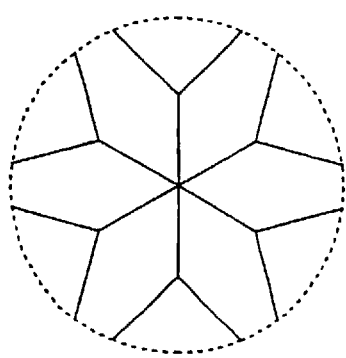
Figure 5:
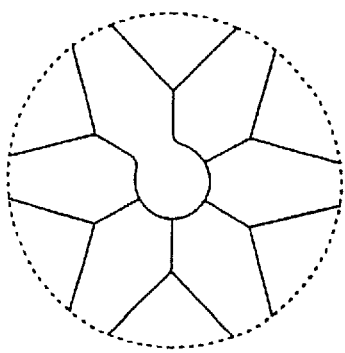

FIGS. 4 and 5 show possible preparations of the separating device in plan views.

Figure 1:
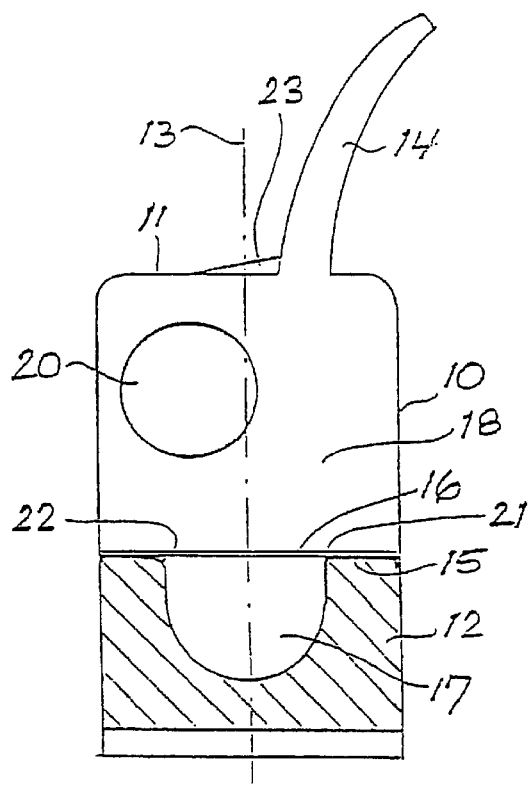
FIG. 1 shows a longitudinal section through a mixing capsule in the starting state.

In accordance with FIG. 1, the mixing capsule comprises a cylindrical cartridge 10 which is closed off at its front end by an end wall 11 and at its rear end by a piston 12. A curved dispensing spout 14 is formed integrally on the end wall 11, eccentrically with respect to the cartridge axis 13. The dispensing spout 14 can be of closable design, for example with a displacement stopper.

The piston 12 has a significant axial wall thickness and is provided with a substantially hemispherical recess which is coaxial with respect to the cartridge axis 13 and is closed off by a separating device 16 attached to the annular front end face 15 of the piston 12. The separating device 16 separates the auxiliary chamber 17, formed by the recess, from the remaining interior of the cartridge, which is referred to here as the main chamber 18.

In the starting state and/or storage state, the main chamber 18 contains a first component, for example in powder form, and the auxiliary chamber 17 contains a second component, for example in liquid form, of the mixture to be produced.

The mixing capsule furthermore includes a freely movable body 20 which is preferably spherical and, in the starting state and/or storage state of the capsule, is situated in the main chamber 18, and the radius of which is slightly smaller than the radius of the hemispherical recess which forms the auxiliary chamber 17. The body 20 and the auxiliary chamber 17 can also have different shapes which deviate from the spherical or hemispherical shape. The term freely movable means that the body can in principle move in all directions without its movement being impeded by any form of guide rails.

The transition between the recess forming the auxiliary chamber 17 and the annular end face 15 of the piston 12 is, as indicated in FIG. 1, sharp-edged over an angular region 21 and rounded in the remaining region 22.

The sharp edge can also be produced by a toothing.

The rounding prevents the separating device from tearing off this end-face inner edge region during the mixing procedure, while the sharp-edged region 21 serves to form an initial tear on the separating device 16.

If, in another embodiment, the edge of the auxiliary chamber 17 is rounded all the way around, the separating device 16 can be made to tear by being preferably overstretched at the desired breaking point as a result of the impact of the body 20 at the start of the mixing procedure.

For use, the mixing capsule, which is supplied by the manufacturer in the condition illustrated in FIG. 1, is placed into a conventional capsule mixer unit with a capsule holder, in which it is made to vibrate, for example, along the cartridge axis 13. In addition to purely translational movements of the capsule, rotary movements are also possible, if appropriate in combination with translational movements. In the process, the body 20 comes into contact with the separating device 16 and penetrates through it. As a result, main chamber 18 and auxiliary chamber 17 are connected to form a common mixing space. During the further mixing procedure, the components are mixed together in this mixing space.

Figure 2:
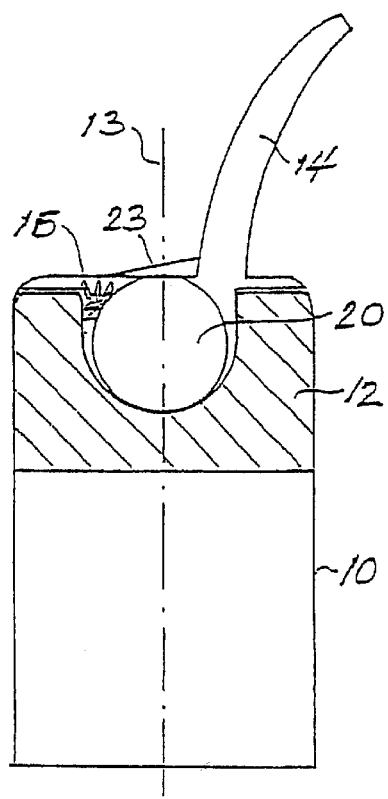
FIG. 2 shows the same capsule at the end of the dispensing procedure.

To dispense the finished mixture, the piston 12 is displaced forward, in a commercially available application instrument, until it reaches the position shown in FIG. 2.

Since the recess which forms the auxiliary chamber 17 is of substantially hemispherical design and has a slightly larger radius than the spherical body 20, this body enters the recess and, in the process, acts as a displacement body. As a result, the mixing space can be emptied substantially completely.

If the auxiliary chamber 17 is arranged coaxially with respect to the cartridge axis 13 and the dispensing spout 14 is arranged eccentrically, the body 20 does not impede the dispensing procedure.

To ensure that parts of the mixture which collect on the opposite side of the body 20 from the dispensing spout also enter the spout 14, at least one channel 23 which deepens toward the dispensing spout 14 can be molded integrally in the end wall 11 of the cartridge 10.

In a further variant (not shown), the dispensing spout 14 can be arranged coaxially with respect to the cartridge axis 13.

So that the body 20 in this embodiment does not block the outlet for the finished mixture, it is preferable for a plurality of channels running in different directions toward the dispensing spout 14 to be formed integrally in the end wall 11 of the cartridge 10.

Figure 3:
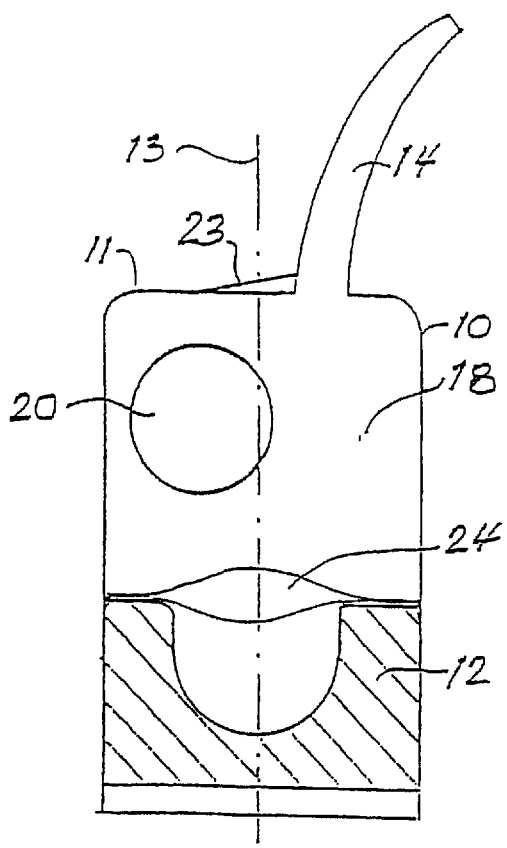
FIG. 3 shows a view, similar to that in FIG. 1, of a different embodiment.

The illustrative embodiment shown in FIG. 3 differs from that shown in FIG. 1 in that a foil cushion 24, comprising two foils, is provided instead of the separating device 16, which cushion can contain a third component.

In a two-component variant, the underside of the cushion 24 can be thermoformed down to the base of the piston. In this way, it is possible to produce an improved diffusion barrier with respect to the piston.

When the mixing procedure begins, the body 20 penetrates through the foil cushion 24, so that all three components can be mixed in the mixing space which is then formed as a combination of main chamber 18 and auxiliary chamber 17.

As is shown in the drawing, the piston 12 has a substantial wall thickness. This has the advantage that the piston 12 presents a good diffusion barrier even if, for cost reasons, it is made from plastic.

FIGS. 4 and 5 show plan views of possible preparations of the separating device 16 which allow the mixing capsule to be activated easily and substantially completely without component parts of the separating device being embedded in the mixed composition during mixing. The preparation is preferably done by preliminary damaging of the foil used for the separating device, for example by radiation.

The mixing capsule is normally used together with a further device. Device within the meaning of the invention is to be understood on the one hand as a unit which is used to activate the mixing capsule, preferably a unit which can set the mixing capsule in translational and/or rotary movement, and, on the other hand, as a device which facilitates the dispensing of the mixed composition from the mixing capsule, preferably a device comprising a ram or a displaceable piston rod.

LIST OF REFERENCE SYMBOLS 10 cartridge
11 end wall
12 piston
13 cartridge axis
14 dispensing spout
15 end face
16 separating device/foil
17 auxiliary chamber
18 main chamber
20 body
21 possible sharp-edged region
22 possible rounded region
23 channel
24 foil cushion

What is claimed is:

1. A mixing capsule assembly, comprising:
   a cartridge,
   a dispensing spout
   a piston which is arranged displaceably in the cartridge,
   a sealed main chamber in said cartridge for receiving a first component,
   an auxiliary chamber which is provided in the piston for receiving a second component,
   at least one freely movable body, and
   a separating device which separates the auxiliary chamber from the main chamber and through which the body can penetrate,
   wherein the body is arranged in the main chamber when the separating device is closed, and
   wherein the auxiliary chamber and the body are designed in such a way that, during a dispensing operation, the body can pass into the auxiliary chamber to serve as a displacement body together with the piston.

2. The mixing capsule assembly as claimed in 1, wherein the mixing capsule assembly has a coding.

3. The mixing capsule as claimed in claim 2, wherein the coding is a visible indicator on at least one part of the mixing capsule assembly.

4. The mixing capsule assembly as claimed in claim 3, which the dispensing spout is mounted so as to be able to swivel or pivot with respect to the cartridge.

5. The mixing capsule assembly as claimed in claim 2, in which the coding is provided by the dispensing spout.

6. The mixing capsule assembly as claimed in claim 2, which the dispensing spout is mounted so as to be able to swivel or pivot with respect to the cartridge.

7. The mixing capsule assembly as claimed in claim 1, in which the dispensing spout is mounted so as to be able to swivel or pivot with respect to the cartridge.

8. The mixing capsule as claimed in claim 1, which the dispensing spout and the cartridge are produced in a two-component injection-molding method.

9. The mixing capsule assembly as claimed in claim 1, in which the body is of spherical design.

10. The mixing capsule assembly as claimed in claim 1, in which the auxiliary chamber has substantially a shape of a hemisphere with a slightly greater radius compared to a cross-section size of the body.

11. The mixing capsule assembly as claimed in claim 1, which the piston is deformable.

12. The mixing capsule assembly as claimed in claim 1, which the separating device adheres to an annular surface of the piston, which piston, delimits the auxiliary chamber, and
   wherein a transition between the annular surface and an inner wall of the auxiliary chamber has a sharp-edged region.

13. The mixing capsule assembly as claimed in claim 12, wherein the transition between the annular surface and an inner wall of the auxiliary chamber is rounded in a remaining region.

14. The mixing capsule assembly as claimed in claim 1, in which the separating device adheres to an annular surface of the piston, which piston, delimits the auxiliary chamber, and
   wherein the transition between the annular surface and an inner wall of the auxiliary chamber is rounded in a remaining region.

15. The mixing capsule assembly as claimed in claim 1, in which the separating device is prepared in advance in order to form at least one desired breaking point.

16. The mixing capsule assembly as claimed in claim 15, in which the advance preparation is one of (i) star-shaped, (ii) branched in a star shape toward an end face of the auxiliary chamber, and (iii) skittle-shaped.

17. The mixing capsule assembly as claimed in claim 1, which the dispensing spout is fitted eccentrically on the main chamber.

18. The mixing capsule assembly as claimed in claim 17, which at least one channel, which opens into the dispensing spout, is formed in an end wall of the main chamber which is provided with the dispensing spout.

19. The mixing capsule assembly as claimed in claim 18, wherein at least one recess is formed in the auxiliary chamber.

20. The mixing capsule assembly as claimed in claim 17, wherein at least one recess is formed in the auxiliary chamber.

21. The mixing capsule assembly as claimed in claim 1, comprising a further chamber for receiving a third component, the further chamber being provided either as a cushion formed in the separating device or being secured in cushion form on an outer wall of the mixing capsule.

22. The mixing capsule assembly as claimed in claim 1, in which the separating device comprises at least one of
   metal-containing foil;
   hydrocarbon-containing layers; and
   ceramic barrier layers, such as $SiO_x$ layers.

23. The mixing capsule assembly as claimed in claim 22, in which the piston comprises materials selected from metal, glass, ceramic, plastic, plastic-coated metal, glass and ceramic, and metalized plastic.

24. The mixing capsule assembly as claimed in claim 23, in which the body comprises materials selected from glass, ceramic, PTFE, plastic-coated metal, and stainless steel.

25. The mixing capsule assembly as claimed in claim 22, in which the body comprises materials selected from glass, ceramic, PTFE, plastic-coated metal, and stainless steel.

26. The mixing capsule assembly as claimed in claim 1, in which the piston comprises materials selected from metal, glass, ceramic, plastic, plastic-coated metal, glass and ceramic, and metalized plastic.

27. The mixing capsule assembly as claimed in claim 26, which the body comprises materials selected from glass, ceramic, PTFE, plastic-coated metal, and stainless steel.

28. The mixing capsule assembly as claimed in claim 1, in which the body comprises materials selected from glass, ceramic, PTFE, plastic-coated metal, and stainless steel.

29. The mixing capsule assembly as claimed in claim 1, which contains, as the first and/or second component, a substance selected from solids and/or liquids.

30. The use of the mixing capsule assembly as claimed in claim 1, for mixing glass ionomer cement dental materials.

31. A mixer unit with a capsule holder, including the mixing capsule assembly as claimed in claim 1.

32. A method for producing a mixing capsule as claimed in claim 1, comprising a two-component injection-molding method.

33. A method for mixing and dispensing mixtures from mixing capsules, comprising the following steps:
   a) provision of a mixing capsule with at least two chambers in which components of a mixture are stored separated from one another by a separating device, comprising a cartridge, a piston arranged displaceably in the cartridge, a dispensing spout, and at least one freely movable body which can penetrate the separating device and can pass as a displacement body into one of the chambers during the dispensing procedure,
   b) insertion of the mixing capsule into a mixer unit with a capsule holder,
   c) acceleration of the mixing capsule by translational and/or rotary movement, as a result of which the at least two chambers separated by a separating device are opened to form one mixing space,
   d) removal of the mixing capsule from the mixer unit, and
   e) displacement of the piston by using an application device with a piston rod, as a result of which the mixture produced in step c) is applied onto a surface via the dispensing spout of the mixing capsule.

34. A method according to claim 33, wherein said mixture is a dental material mixture.

35. A method according to claim 33, wherein said mixture is a glass ionomer cement dental material mixture.

36. A mixing capsule assembly for dental material mixtures comprising:
   a cartridge;
   a main chamber in said cartridge for receiving a first dental material component;
   a piston displaceably supported in the cartridge;
   an auxiliary chamber in the piston for receiving a second dental material component;
   a freely movable body in said main chamber; and
   a separator separating the auxiliary and main chambers during storage of said mixing capsule assembly,
   wherein the body, auxiliary chamber and separator are configured such that predetermined mixing movements of said capsule assembly, independent of any movement of the piston, cause said body to penetrate said separator and facilitate mixing of said first and second dental material components, and
   wherein the body and auxiliary chamber are configured such that said body moves into the auxiliary chamber to form a displacement body assembly together with the piston to facilitate dispensing of the mixture from the cartridge upon movement of the piston after completion of mixing operation.

* * * * *

UNITED STATES PATENT AND TRADEMARK OFFICE
CERTIFICATE OF CORRECTION

PATENT NO. : 6,715,645 B2
DATED : April 6, 2004
INVENTOR(S) : Peuker, Marc

It is certified that error appears in the above-identified patent and that said Letters Patent is hereby corrected as shown below:

Column 3,
Lines 18 and 29, delete "As" and insert -- If --, therefor.

Column 4,
Line 45, delete "As" and insert -- If --, therefor.

Column 6,
Line 30, delete "metalized" and insert -- metallized --, therefor.

Column 7,
Lines 17 and 23, delete "contemplated" and insert -- conceivable --, therefor.

Column 8,
Line 8, after "opening." insert -- Preferred illustrative embodiments of the mixing capsule are explained below with reference to the drawings. -- as a new paragraph.

Column 10,
Lines 51, 56 and 61, insert -- in -- before "which".

Column 11,
Lines 4, 6, 29, 32 and 66, insert -- in -- before "which".
Lines 54 and 64, delete "metalized" and insert -- metallized --, therefor.

Signed and Sealed this

Sixth Day of September, 2005

JON W. DUDAS
*Director of the United States Patent and Trademark Office*